United States Patent [19]

Gosswein

[11] Patent Number: 4,865,847

[45] Date of Patent: Sep. 12, 1989

[54] GASTRIC MUCOSA PROTECTIVE AGENTS

[75] Inventor: Claus Gosswein, Buchholz, Fed. Rep. of Germany

[73] Assignee: Code Kaffee-Handelsges. mbH, Hamburg, Fed. Rep. of Germany

[21] Appl. No.: 123,854

[22] PCT Filed: Feb. 3, 1987

[86] PCT No.: PCT/EP87/00052

§ 371 Date: Dec. 4, 1987

§ 102(e) Date: Dec. 4, 1987

[87] PCT Pub. No.: WO87/04619

PCT Pub. Date: Aug. 13, 1987

[51] Int. Cl.$^4$ .............................................. A61K 47/00
[52] U.S. Cl. .................................... 424/439; 424/471; 424/474; 424/475; 424/481; 424/195.1
[58] Field of Search ................. 424/439, 195.1, 439, 424/481, 475, 474; 426/419

[56] References Cited

U.S. PATENT DOCUMENTS 4,003,999  1/1977  Lybrand et al. ................. 424/195.1

Primary Examiner—Thurman K. Page
Assistant Examiner—Leon R. Horne
Attorney, Agent, or Firm—Cushman, Darby & Cushman

[57] ABSTRACT

Isolated chlorogenic acid or the physiologically acceptable derivatives thereof when used before or simultaneously with the administration of gastric acid secretion-stimulating and/or gastric mucosa-irritating or attacking foods, beverages and/or medicaments lead to a reduction of gastric acid secretion and/or to the protection of the gastric mucosa.

8 Claims, No Drawings

GASTRIC MUCOSA PROTECTIVE AGENTS

It is known that duodenal ulcers, ventricular ulcers and other gastric mucosa lesions, which are frequently induced by stress and/or medicaments, can bleed and perforate in a life-threatening manner.

It is also known that various foods, beverages and in particular medicaments irritate the gastric mucosa and in higher concentrations even attack the same, so that this can also lead to ulceration and bleeding. Gastric mucosa-irritating beverages are e.g. alcohol and strongly roasted coffee. The irritation is frequently based on a stimulation of gastric acid secretion. Certain drug or medicament groups, e.g. non-steroidal antirheumatics (NSAID) have a clearly defined side-effect spectrum, particularly undesired gastrointestinal effects (e.g. gastric mucosa lesions, associated with bleeding or perforation). Thus, it has been observed that acetylsalicylic acid can lead to gastrorrhagia, which also applies for other NSAID's, such as e.g. indomethacin (cf. R. Bruhn et al, Fortschritte der Medizin, 100 (36), pp 1661 to 1668 (1982). There is a definite risk linked with therapy with acetylsalicylic acid and other medicaments from the NSAID group, so that before using these medicaments, their therapeutic usefulness must be balanced against the accompanying risk.

It is an object of the present invention to find an agent protecting the gastric mucosa against the development of ulcerations in such a way that gastric mucosa-harming foods, beverages and/or medicaments can be administered or taken without disturbing side-effects extending up to life-threatening bleeding and perforation.

It has been found that this problem can be solved in that isolated chlorogenic acid or its physiologically acceptable derivatives are suitable for protecting the gastric mucosa against foods, beverages and/or medicaments, which are known to damage the gastric and duodenal mucosa or which can stimulate gastric acid secretions. According to the invention the tanning agents or] chlorogenic is are administered before or simultaneously with the intake of said irritating materials.

Within the scope of the invention the term chlorogenic acid is understood to mean the mono- and di-caffeoylquinic acids, as well as mixtures thereof. Particular preference is given to 3-, 4- and 5-caffeoylquinic acids or mixtures thereof and in particular 3-caffeoylquinic acid. The acids can be used as free acid or in the form of their physiologically acceptable derivatives, particularly salts or esters. Alkali metal salts and in particular potassium salts are particularly suitable. These derivatives can be used in place of the free acid, because the acid is liberated therefrom in the strongly acid gastric medium.

Chlorogenic acid is a compound occurring in numerous plants, e.g. in green coffee beans, was isolated by Freudenberg in 1920, its structure was explained and was subsequently also synthesized (cf. Merck Index, tenth edition, No. 2112). It is known from a publication by V. Istudor et al, Farmacia, 29, pp 41 to 48 (1981) that an extract obtainable from Calendulae flores can be used in tea form for treating gastric and gastroduodenal ulcers. It was reported that the extract contains inter alia alantoin, caffeine acid and polyphenol derivatives, including chlorogenic acid. Chlorogenic acid is said to be a choleretic and cholagogue. A synergism is assumed between the different constituents of the tested extract.

It has now been found that as a pure substance chlorogenic acid has an action which protects the gastric mucosa. This is clearly due to the fact that under the action of chlorogenic acid a surface-protecting film is formed, which protects the gastric mucosa. There is a simultaneous reduction in stimulated gastric acid secretion. These effects are possibly based on an adstringent action of chlorogenic acid.

Chlorogenic acid is able to protect the gastric or duodenal mucosa against aggressive or acid secretion-stimulating foods, beverages and medicaments. As has been gastroscopically observed, immediately after contact with the mucosa the agents of the invention form a whitish net-like coating, which acts in the manner of a protective film. On applying 10% alcohol as the irritant, there is no change in the thus protected region, whereas the untreated gastric mucosa has a pathological redness. Similar tests with acetylsalicylic acid also provide an effective protection against the gastric mucosa, whilst simultaneously preventing the much feared bleeding otherwise observed when administering alone acetylsalicylic acid or other NSAID's.

For inventive use, the chlorogenic acid is preferably formulated in such a way that release only takes place in the stomach. This can take place in per se known manner in that during the preparation of the tablets use is made of a coating, which only dissolves in the acid gastric medium. These agents are administered either before or preferably simultaneously with those products against which the gastric mucosa is to be protected. In the case of foods or beverages, they inherently contain substantially no chlorogenic acid or an inadequate quantity thereof and which as a result of the addition according to the invention can be brought into a more stomach-friendly form.

Particular significance is attached to the invention in connection with pharmaceutically active substances, which damage the gastric mucosa to such an extent that ulcers or bleeding can occur. A particular problem is caused in this connection by acetylsalicylic acid and other NSAID's, which are taken by many patients on a regular basis as analgesics and antirheumatics and can then lead to the described side-effects in the digestive tract. Through using a combined product formed from acetylsalicylic acid or any of the other NAID's with chlorogenic acid in an administration form which only releases the active substances in the gastric juice, the gastric mucosa can be effectively protected, so that there are no longer gastric mucosa lesions or bleeding. In a particularly favourable administration form, e.g. as a core/shell tablet with the active substance as the core and the protective substance (chlorogenic acid) in the outer shell, firstly the chlorogenic acid is released and then the active substance.

The following comparative tests serve to further illustrate the invention. Coffee was used as the gastric acid secretion-stimulating and gastric mucosa-irritating beverage. Coffee sample 1 only had the residual chlorogenic acid content still present in roasted coffee after roasting, whereas the remaining coffee types contained a chlorogenic acid addition in accordance with the invention.

PHYSIOLOGICAL TESTS

The influence of coffee samples 1 to 5 on the human gastric acid secretion was investigated in a test series. The samples differ only as regards the chlorogenic acid content, as shown in table 1. Each test subject received approximately 250 ml of the individual coffee types in a random double-blind crossover arrangement. The test subjects were healthy males and females aged between 19 and 35. After fasting for 12 hours, in the morning the test subjects were fitted up with a naso-gastral probe, via which the gastric juice was initially quantitatively removed at time $t_0$. For determining the basal acid secretion of the new formed gastric juice, during the following 60 minutes $t_{0-60}$ quantitative removal took place at 15 minute intervals. On five different test days, which were at least two days apart, the test subjects received in each case 250 ml of coffee samples 1 to 5. Before the test subjects ingested the different coffee samples within 10 minutes, there was initially a return of the gastric juice removed at time 0. 5 ml of gastric juice was removed both 10 and 30 minutes after the start of coffee drinking using the aforementioned probe. A quantitative removal of the gastric juice then took place at 15 minute intervals between the 30th and 150th minute. The titratable acid in these samples was determined with 0.1n NaOH. Table 2 gives the values obtained in ml of NaOH. The volume of the removed gastric juice is given in ml in table 2.

The period $t_{60-150}$ was used for the comparative evaluation of the results, because as is known various other effects are superimposed during the first 60 minutes after ingestion. The values found were obtained by intraindividual evaluation, the dispersion according to the following equation was calculated for the mean values:

$$SEM = \sqrt{\frac{(x_i - x)^2}{N(N-1)}}$$

$x_i$ = individual measurement
$x$ = mean value of measured values
$N$ = number of measured values Coffee samples 1 to 5 had an identical degree of roasting, but contained rising chlorogenic acid quantities. As is apparent from the results of table 2, coffee 1 led to the highest acid stimulation and there was a significant decrease in gastric acid secretion with rising chlorogenic acid content. Volume secretion also decreased in the order of coffee types 1 to 5. The influence of chlorogenic acid on the reduction of human gastric acid secretions stimulated by coffee roasting substances is readily apparent.

TABLE 1

| Coffee No. | Chlorogenic acid content mg/100 ml of coffee |
|---|---|
| 1 | 110.0 |

TABLE 1-continued

| Coffee No. | Chlorogenic acid content mg/100 ml of coffee |
|---|---|
| 2 | 134.3 |
| 3 | 156.8 |
| 4 | 178.1 |
| 5 | 188.1 |

TABLE 2

Cumulative gastric acid secretion and gastral volume secretion between 60 and 150 minutes after drinking coffee (250 ml of coffees 1 to 5) in 10 healthy test subjects (intraindividual evaluation)

| Coffee No. | Gastric acid secretion | | Gastral volume secretion | |
|---|---|---|---|---|
| | $t_{60-150}$ | Percentage increase compared with coffee 5 | $t_{60-150}$ | Percentage increase compared with coffee 5 |
| 5 $\bar{x}$ SEM | 36.6 ± 6.70 | | 69.8 ± 8.29 | |
| 4 $\bar{x}$ SEM | 39.4 ± 6.91 | 8.5%/5 | 77.8 ± 8.66 | 11% |
| 3 $\bar{x}$ SEM | 51.0 ± 8.49 | 39%/5 | 87.2 ± 11.23 | 25% |
| 2 $\bar{x}$ SEM | 53.2 ± 13.62 | 45%/5 | 90.6 ± 19.16 | 30% |
| 1 $\bar{x}$ SEM | 64.5 ± 5.96 | 76%/5 | 101.1 ± 8.28 | 45% |

I claim:
1. A method for reducing gastric acid secretion and/or for protecting the gastric mucosa which comprises administering isolated chlorogenic acid or the physiologically acceptable derivatives thereof before or simultaneously with the administration of gastric acid secretion-stimulating and/or gastric mucosa-irritating or attacking foods, beverages and/or medicaments.

2. Food, beverage or medicament which contains a gastric acid secretion-reducing and/or gastric mucosa-protecting quantity of chlorogenic acid.

3. Product according to claim 2 which contains physiologically acceptable derivatives of chlorogenic acid.

4. Product according to claim 2 which contains the additive in an effect, but not harmful dose.

5. Product according to claim 2 which contains a non-steroidal antirheumatic as active medicinal substance.

6. Product according to claim 2 which contains acetylsalicylic acid as the active medicinal substance.

7. Medicament according to claim 2 characterized in that it is in the form of an orally administrable tablet, which contains in the core the active medicinal substance and in the shell the chlorogenic acid.

8. Medicament according to claim 2 characterized in that it is in the form of an orally administrable tablet having a coating which only dissolves in the acidic gastric medium.

* * * * *